US00PP11916P2

(12) United States Plant Patent
Trees

(10) Patent No.: US PP11,916 P2
(45) Date of Patent: Jun. 12, 2001

(54) NEW GUINEA IMPATIENS PLANT NAMED 'BALCEBHOPI'

(75) Inventor: Scott C. Trees, Nipomo, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 09/475,970

(22) Filed: Dec. 31, 1999

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Balcebhopi', characterized by its dark pink-colored flowers; upright and mounded plant habit; good basal branching; and dark green leaves.

1 Drawing Sheet

BACKGROUND OF THE INVENTION

The present invention relates to a new and distinct cultivar of New Guinea Impatiens plant, botanically known as *Impatiens hawkeri* and hereinafter referred to by the cultivar name Balcebhopi.

The new Impatiens is a product of a planned breeding program conducted by the Inventor in Arroyo Grande, Calif. The objective of the breeding program was to develop new compact cultivars with freely-branching growth habit, numerous large flowers, and attractive flower and foliage colors.

The new Impatiens originated from a cross made by the Inventor of the *Impatiens hawkeri* cultivar Grenada, disclosed in U.S. Plant Pat. No. 9,343, as the male, or pollen parent, with the proprietary selection of *Impatiens hawkeri* identified as code No. 916 as the female, or seed parent. The cultivar Balcebhopi was discovered and selected by the Inventor as a flowering plant within the progeny of the stated cross in a controlled environment in Arroyo Grande, Calif. in 1997. Plants of the new Impatiens and the cultivar Grenada differ primarily in flower color.

Asexual reproduction of the new cultivar by terminal cuttings taken at Arroyo Grande, Calif., has shown that the unique features of this new Impatiens are stable and reproduced true to type in successive generations of asexual reproduction.

SUMMARY OF THE INVENTION

The following traits have been repeatedly observed and are determined to be the unique characteristics of 'Balcebhopi'. These characteristics in combination distinguish 'Balcebhopi' as a new and distinct cultivar:

1. Dark pink-colored flowers.
2. Upright and mounded plant habit.
3. Good basal branching.
4. Dark green leaves.

The new Impatiens can be compared to the cultivar, BFP-368 Rose, disclosed in U.S. Plant Pat. No. 9,532. However, in side-by-side comparisons conducted by the Inventor in Arroyo Grande, Calif., plants of the new Impatiens differ from plants of the cultivar BFP-368 Rose in the following characteristics:

1. Plants of the new Impatiens are more taller and more vigorous than plants of the cultivar BFP-368 Rose.
2. Plants of the new Impatiens and the cultivar BFP-368 Rose differ in stem color.
3. Plants of the new Impatiens have larger leaves with longer petioles than plants of the cultivar BFP-368 Rose.
4. Plants of the new Impatiens are not as freely flowering as plants of the cultivar BFP-368 Rose.

BRIEF DESCRIPTION OF THE PHOTOGRAPH

The accompanying photograph illustrates the overall appearance of the new cultivar as true as it is reasonably possible to obtain in colored reproductions of this type. Colors in the photographs may differ slightly from the color values cited in the detailed botanical description which more accurately describe the actual colors of the new Impatiens. The photograph comprises a top perspective view of a typical flowering plant of 'Balcebhopi'.

DETAILED BOTANICAL DESCRIPTION

The cultivar Balcebhopi has not been observed under all possible environmental conditions. The phenotype may vary somewhat with variations in environment such as temperature and light intensity, without, however, any variance in genotype. The following observations and measurements describe plants about 10 weeks after planting rooted cuttings and grown 10-cm pots in West Chicago, Ill., under commercial practice in a double-layered acrylic-covered greenhouse with day temperatures about 21° C., night temperatures about 19° C., and light levels about 2,500 to 3,500 footcandles.

In the following description, color references are made to The Royal Horticultural Society Colour Chart except where general terms of ordinary dictionary significance are used.

Botanical classification: *Impatiens hawkeri* cultivar Balcebhopi.

Parentage:

*Male parent.*—*Impatiens hawkeri* cultivar Grenada, disclosed in U.S. Plant Pat. No. 9,343.

*Female parent.*—Proprietary selection of *Impatiens hawkeri* identified as code No. 916, not patented.

Propagation:

*Type cutting.*—Terminal cuttings.

*Time to initiate roots.*—About 7 days with 18° C.

*Time to develop roots.*—About 21 days with 18° C.

*Root description.*—Fibrous, fine, freely branching.

Plant description:

*Plant form.*—Upright and mounded.

*Growth and branching habit.*—Vigorous. Good basal branching, dense and bushy growth. Appropriate for 10 and 12.5-cm containers.

*Crop time.*—About 8 to 10 weeks are required to produce a finished flowering plant from a rooted cutting.

*Plant height.*—About 15.9 cm.

*Plant diameter.*—About 18 cm.

*Lateral branches.*—Diameter: About 7 mm. Internode length: About 3.6 cm. Color: 144A overlaid with 184A.

*Foliage description.*—Leaves simple, generally symmetrical, abundant, in whorls or opposite. Length: About 10.1 cm. Width: About 4.3 cm. Shape: Lanceolate. Apex: Acute. Base: Attenuate. Margin: Serrulate with ciliation. Texture: Smooth, glabrous. Color: Fully expanded leaves, upper surface: 147A. Fully expanded leaves, lower surface: 148B. Venation, upper surface: 144A. Venation, lower surface: 184A. Petiole: Length: About 1.8 cm. Diameter: About 3 mm. Color: 144A overlaid with 184A.

Flower description:

*Flower type and habit.*—Dark pink-colored flowers. Freely and continuously flowering. Flowers arise from leaf axils. Usually about five flowers and flower buds per lateral branch. Flowers positioned mostly above the foliage and typically face upright and outward. Flowers roughly rounded in shape. Flowers persistent, iridescent.

*Flowering season.*—Year-round under greenhouse conditions. In the garden, flowering is continuous from spring until fall.

*Flower size.*—About 6.3 cm.

*Flower buds.*—Length: 1.8 cm., Diameter: 1.1 cm., Shape: Ovoid, Color: Close to 57A.

*Petals.*—Quantity: Five, imbricate. Length: Upper petal, about 2.7 cm; lower petals, about 3.3 cm. Width: Upper petal, about 4.4 cm; lower petals, about 3.3 cm. Shape: Obovate to obcordate. Apex: Emarginate. Base: Attenuate. Margin: Entire. Texture: Smooth. Color: Fully opened, upper surface: Closest to 57A; whitish, close to 155D at base of petals. Fully opened, lower surface: 57D.

*Spur.*—Length: About 4.6 cm. Shape: Narrow and curved. Color: 185A.

*Peduncles.*—Length: About 5 cm. Angle: Erect. Strength: Strong. Color: 144C overlaid with 184A.

*Reproductive organs.*—Androecium: Stamen number: Five, anthers fused, filaments free. Anther shape: Obovate. Anther length: About 3 mm. Amount of pollen: Moderate. Pollen color: 11C. Gynoecium: Five-loculate fused. Pistil length: About 5 mm. Style length: About 3 mm. Style color: 144C. Stigma color: 144D. Ovary color: 144A.

Disease resistance: Under commercial conditions, resistance to pathogens common to New Guinea Impatiens has not been observed.

Seed development: Seed production has not been observed.

It is claimed:

1. A new and distinct cultivar of New Guinea Impatiens plant named 'Balcebhopi', as illustrated and described.

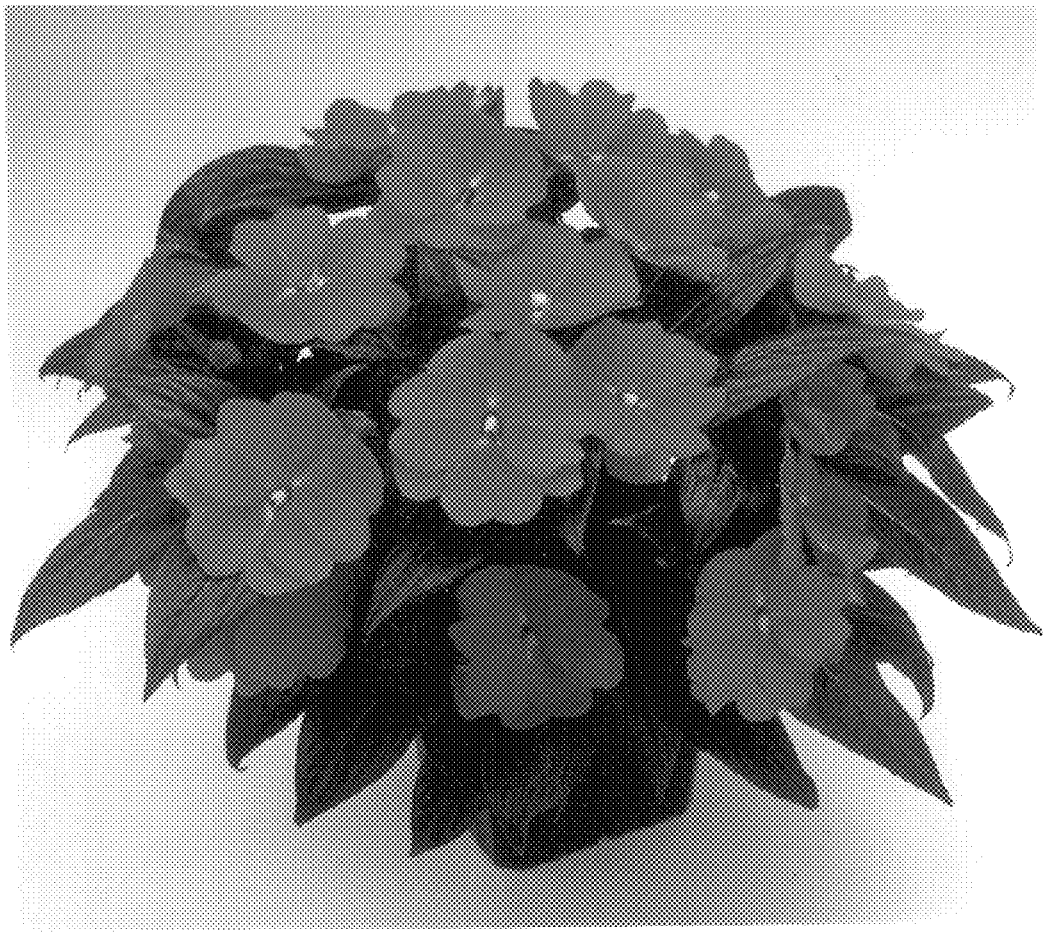

* * * * *